United States Patent [19]

Schweizer et al.

[11] 4,315,825

[45] Feb. 16, 1982

[54] LITHIUM SOAPS OF SUBSTITUTED HYDROXYLATED FATTY ACIDS AND THEIR USE AS THICKENING AGENTS

[75] Inventors: Dieter Schweizer, Düsseldorf; Johann Glasl, Solingen, both of Fed. Rep. of Germany

[73] Assignee: Henkel Kommanditgesellschaft auf Aktien, Dusseldorf-Holthausen, Fed. Rep. of Germany

[21] Appl. No.: 165,744

[22] Filed: Jul. 3, 1980

[30] Foreign Application Priority Data

Jul. 9, 1979 [DE] Fed. Rep. of Germany ....... 2927686

[51] Int. Cl.$^3$ ............................................. C10M 5/14
[52] U.S. Cl. ..................................... 252/41; 260/413
[58] Field of Search ....................... 252/41; 260/413 S

[56] References Cited

U.S. PATENT DOCUMENTS

| 2,651,616 | 9/1953 | Matthews et al. | 252/41 |
| 2,841,557 | 7/1958 | Nelson | 252/41 |
| 3,000,823 | 9/1961 | Clarke et al. | 252/41 X |
| 3,009,878 | 11/1961 | Eckert | 252/41 |
| 3,036,970 | 5/1962 | Morway et al. | 252/41 X |
| 3,313,828 | 4/1967 | Szczepanek | 252/41 X |
| 3,884,820 | 5/1975 | Miller et al. | 252/41 |
| 3,985,662 | 10/1976 | Campbell et al. | 252/41 |
| 4,110,233 | 8/1978 | Bailey et al. | 252/41 |

FOREIGN PATENT DOCUMENTS

| 927965 | 6/1963 | United Kingdom | 252/41 |
| 987573 | 3/1965 | United Kingdom | 252/41 |
| 1030700 | 5/1966 | United Kingdom | 252/41 |

Primary Examiner—Andrew Metz
Attorney, Agent, or Firm—Hammond & Littell, Weissenberger and Muserlian

[57] ABSTRACT

Lithium soaps of non-terminal vicinal substituted fatty acids having from 16 to 22 carbon atoms wherein said vicinal substitution is a hydroxy group and a group selected from the group consisting of alkoxy having from 1 to 18 carbon atoms, alkenoxy having from 3 to 18 carbon atoms, and mixtures thereof, alkanoyloxy having from 1 to 18 carbon atoms, alkenoyloxy having from 3 to 18 carbon atoms, and mixtures thereof, said fatty acid being substituted with from 0 to 2 other hydroxyls; as well as lubricating greases containing said lithium soaps.

12 Claims, No Drawings

LITHIUM SOAPS OF SUBSTITUTED HYDROXYLATED FATTY ACIDS AND THEIR USE AS THICKENING AGENTS

BACKGROUND OF THE INVENTION

The lithium soap of 12-hydroxystearic acid (lithium hydroxystearate) is frequently used in lubricating greases as a thickening agent. 12-Hydroxystearic acid is prepared from ricinoleic acid by hydrogenation of the double bond. This step requires the use of autoclaves or other pressure equipment that are expensive and need extensive maintenance. In addition, all precautions required for work with hydrogen must be observed. A further disadvantage is the frequently strong fluctuation in price to which ricinoleic acid is subject.

OBJECTS OF THE INVENTION

An object of the present invention is the making available of a class of new, substituted hydroxylated lithium soaps that can be used as thickening agents in lubricating greases in diverse ways.

Another object of the present invention is the development of readily accessible lithium soaps not subject to market fluctuation of the starting material.

A further object of the present invention is to develop lithium soaps with controlled thickening effect by varying the substitutions thereon. Thus the invention is intended to influence finally certain properties of the lubricating greases by selection and adaptation of the desired constitution of a lithium soap in the sense of the invention and thereby making possible an increased adaptability of the properties of the lubricating greases to the desired purpose.

A yet further object of the present invention is the obtaining of lithium soaps of non-terminal vicinal substituted fatty acids having from 16 to 22 carbon atoms wherein said vicinal substitution is a hydroxy group and a group selected from the group consisting of alkoxy having from 1 to 18 carbon atoms, alkenoxy having from 3 to 18 carbon atoms, and mixtures thereof, alkanoyloxy having from 1 to 18 carbon atoms, alkenoyloxy having from 3 to 18 carbon atoms, and mixtures thereof, said fatty acid being substituted with from 0 to 2 other hydroxyls.

These and other objects of the invention will become more evident as the description thereof proceeds.

DESCRIPTION OF THE INVENTION

The above objects have been achieved according to the present invention. The invention is based on the surprising observation that lithium soaps of certain vicinally substituted hydroxycarboxylic acids possess a pronounced thickening effect in lubricants or lubricating grease and that especially the final substance parameters of the lubricating grease are strongly influenced by the variation of the substituents on the hydroxycarboxylic acid.

Consequently, the solution of the invention is, in a first form of execution, new lithium soaps of non-terminal monohydroxylated and/or polyhydroxylated saturated and/or unsaturated fatty acids with 16 to 22 carbon atoms, which are substituted, vicinal to at least one hydroxyl group, with a straight-chain or branched, and optionally, unsaturated, alkoxy or acyloxy radical with up to 18 carbon atoms.

More particularly, the invention in the first form of execution, relates to lithium soaps of non-terminal vicinal substituted fatty acids having from 16 to 22 carbon atoms wherein said vicinal substitution is a hydroxy group and a group selected from the group consisting of alkoxy having from 1 to 18 carbon atoms, alkenoxy having from 3 to 18 carbon atoms, mixtures of said alkoxy and said alkenoxy, alkanoyloxy having from 1 to 18 carbon atoms, alkenoxyloxy having from 3 to 18 carbon atoms, and mixtures of said alkanoyloxy and said alkenoxyloxy, said fatty acid being substituted with from 0 to 2 other hydroxyls.

The invention also concerns in another form of execution the use of these new lithium soaps as thickening agents in lubricating oils or lubricating greases. Finally, lubricating greases with the usual lubricating agent bases that are liquid at normal temperature, and which were thickened by the incorporation of the above-mentioned new lithium soaps, are a further concern of the invention.

The novel lithium soaps of the present invention can be further depicted by the formula

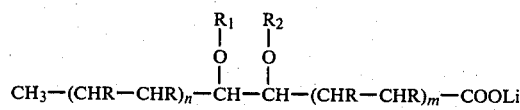

wherein R represents a member selected from the group consisting of hydrogen, hydroxy, a double bond with the adjacent R and mixtures thereof, n is an integer from 0 to 6, m is an integer from 0 to 6, n+m is an integer from 6 to 9, and $R_1$ and $R_2$ represent a member selected from the group consisting of hydrogen, alkyl having from 1 to 18 carbon atoms, alkenyl having from 3 to 18 carbon atoms, alkanoyl having from 1 to 18 carbon atoms and alkenoyl having from 3 to 18 carbon atoms, with the proviso that either $R_1$ or $R_2$ is hydrogen and the further proviso that no more than 3 hydroxy groups or 2 double bonds are present.

The internally or non-terminal mono- or polyhydroxylated saturated and/or unsaturated fatty acids with 16 to 22 carbon atoms, which are substituted, vicinal to at least one hydroxyl group, with a straight-chain or branched, and unsaturated if desired, alkoxy or acyloxy radical, are obtained in a simple manner. They are obtained, for example, by epoxidation of the double bond of non-terminally unsaturated carboxylic acids of the given chain length with subsequent opening of the epoxide ring by reaction with carboxylic acids or alcohols. The hydroxycarboxylic acids with vicinal substitution according to the invention to be used for the preparation of the lithium soap can also be prepared in other known manners, as long as they possess the structural characteristics mentioned.

In a preferred form of preparation of the invention the new lithium soaps are derived from mono- and/or polyunsaturated monocarboxylic acids with 16 to 22 carbon atoms that are obtained from natural substances, as fatty acids. Tallow and or vegetable oils are a preferred source of higher unsaturated carboxylic acids of the given range of carbon atoms. For this purpose previously isolated, defined unsaturated carboxylic acids of the mentioned type may be used, but it is also possible to use mixtures of acids.

The respective starting materials for the preparation of the hydroxycarboxylic acids with vicinal substitution usually possess 1 to 3 double bonds, but the optional presence of additional, small amounts of fatty acids with a higher degree of unsaturation, in mixture, does not interfere. The unsaturated carboxylic acids used as starting material do not have to be substituted or can be substituted with one hydroxyl group, as in the case of ricinoleic acid, for example. Unsaturated $C_{18}$-acids, mainly oleic acid, linoleic acid, linolenic acid and ricinoleic acid, have a special significance. However, brassidic acid, a $C_{22}$-acid, may also be mentioned as a starting material that is relatively easy to obtain.

The epoxidation of such unsaturated acids is known and can be achieved for example with percarboxylic acid or $H_2O_2$ metal salts. The epoxides are easily prepared in high yields at temperatures between 20° and 100° C. and atmospheric pressure, under suitable reaction conditions. The position of the double bond has no significance. In the presence of several double bonds in the molecule, one or several double bonds may be epoxidized. The U.S. Pat. No. 2,485,160 as well as Chemical Week, April 1963, pages 55–60 and 64, may be refered to, for example, for the state of the art as published with respect to epoxidation.

The epoxide ring of the epoxy carboxylic acids obtained in this manner can be opened with acids as well as with alcohols. These reactions are also known in principle; see, for example, Chemical Abstracts, Vol. 56, 2400i–2401a (ring opening of the epoxide with organic acids) as well as Bull, Jap. Petrol. Ind. 7, 25–30 (1965), particularly pages 26 and 27 (ring opening with alcohols).

The opening of the epoxide ring with acids or alcohols generally is carried out without pressure. Yields from 95% to 100% can be obtained in many cases with the use off suitable acid or basic catalysts.

The acid opening of the previously formed epoxide ring(s) for the preparation of the lithium soaps of hydroxycarboxylic acid with vicinal substitution, the final objective of the invention, can be achieved with saturated or unsaturated straight-chain or branched monocarboxylic acids with up to 18 carbon atoms. Preferred are respective carboxylic acids with at least 2 carbon atoms, and it has been observed that the thickening effect of the lithium soap increases also with increasing molecular weight in the case of the acyloxy substitution vicinal to the internal hydroxy group, which is achieved in this instance. Thus monocarboxylic acids, particularly alkanoic acids with larger numbers of carbon atoms within the given range, for example, those of $C_{10}$–$C_{18}$, are particularly suitable for the preparation of lubricating greases of increasingly stiffer character. The following example illustrates this tendency:

The lithium soap of a reaction product of epoxystearic acid with caprylic acid ($C_8$) produces a lubricating grease from a mineral oil base with 10% thickening agent with a resting penetration (DIN 51804) of 411. The corresponding lithium salt from the reaction of epoxystearic acid with stearic acid ($C_{18}$), in contrast, produces a resting pentration of 163 under comparable conditions.

When the primarily formed epoxide product is reacted with alcohols to open the ring, again straight-chain or branched and, if desired, unsaturated alcohols up to 18 carbon atoms may be used. Here alkanols with the chain length range of $C_1$–$C_{12}$, and preferably of $C_2$–$C_8$, proved to be particularly favorable. The lithium soaps obtained by saponification of the alcohol adducts with methyl epoxystearate generally produced softer lubricating greases than those of the previously mentioned carboxylic acid adducts. It is interesting in this event that the adducts of lower alcohols show a greater thickening effect than the adducts of higher alcohols. For example, the lithium soap obtained from the adduct of methyl epoxystearate with n-dodecanol produces a resting penetration of 395 under the abovementioned standard conditions, while the corresponding adduct with n-butanol produces a resting penetration of 306. Furthermore, a considerable variation in the dripping point can be achieved especially with these alkoxy-substituted hydrocarboxylic acid soaps. Which is, for example, rather high for the above-mentioned butanol reaction product, having a value of 186° C. Universally usable lubricating greases, which are characterized, for example, by a wide range of ductility even at low temperature and also a sufficiently high dripping point, can be produced according to the invention by adapting to the respective intended purpose.

The thickening effect, which can be adjusted according to the invention, is produced, as in the case of the lithium hydroxystearate, by the lithium soaps and not by the respective vicinally substituted hydroxycarboxylic acids. The lithium soap can be incorporated into the lubricating grease within the framework of the invention, analogous to the preparation of lubricating greases based on 12-hydroxystearic acid. For example, the hydroxycarboxylic acid substituted with alkoxy and/or acyloxy groups or a corresponding mixture of hydroxycarboxylic acids as is or in the form of an active derivative, especially as ester, can at first be worked into the lubricating grease base to be thickened and then converted into the lithium soap in situ. At first moderately elevated temperatures can be used for the formation of the lithium soaps, up to 100° C., preferably from 70° to 100° C., followed by a final step with higher temperatures for the complete melting of the formed soaps and their homogeneous distribution in the lubricating grease. The temperature preferably exceeds the dripping point of the formed lubricating grease by 10° to 50° C. The liquid lubricating oil base may be added in increments to the reaction mixture.

The use of free hydroxycarboxylic acid with vicinal substitution for the subsequent formation of the lithium soap can be particularly suitable for the preparation of the lithium soaps of hydroxycarboxylic acids with vicinal acyloxy substituents entirely to prevent an uncontrolled ester cleavage at an undesired site, that is at the vicinal acyloxy radical. The substituted hydroxycarboxylic acid is then converted according to the general rule, in situ, in the liquid lubricating agent with a suitable lithium compound. Lithium hydroxide or an aqueous lithium hydroxide solution is used as particularly suitable lithium compound. Preferably lithium hydroxide monohydrate (LiOH.H$_2$O) is employed.

Especially suitable as active derivative of the hydroxycarboxylic acids with vicinal substitution for the saponification with lithium compounds are respective esters, particularly where the vicinal substitution is the alkoxy group. Esters of the substituted carboxylic acids with alcohols with up to 8 carbon atoms generally are preferred. When the in situ saponfication in the lubricating agent is desired, the use of esters of lower alkanols, particularly $C_1$ to $C_3$, can be especially suitable. The removal of the alcohol released during the cleavage of the ester is simple in these cases during the saponification of the hydroxycarboxylic acid ester with vicinal substitution in situ in the liquid lubricating agent. When working at the above temperature, the $C_1$ to $C_3$ alkanols distill off. The working with esters of the substituted hydroxycarboxylic acids can offer certain advantages over the use of the respective free acids. For example, an undesirable condensation of the hydroxycarboxylic acid with itself can be suppressed with the use of esters.

The lubricating agents according to the invention may contain lithium soaps of certain individual hydroxycarboxylic acids with vicinal substitution or mixtures of different lithium soaps of the mentioned type. A variation in the constitution of the soaps present in the mixture with respect to several factors is then possible. For example, mixtures of lithium soaps are produced by the use of various mono- and/or polyunsaturated fatty acids with 16-22 carbon atoms, as mentioned above. However, the mixture of soaps with different acyloxy and/or alkoxy radicals, used instead of this variation and/or in combination with it, is also within the scope of the procedure according to the invention. Since each of the given lithium soaps has its own characteristic combination of thickening effects, it becomes apparent that the range of possible combination made available within the scope of the procedure for the preparation of thickened lubricating greases according to the invention is quite broad.

The concentration of the lithium soap or the mixture of lithium soaps according to the invention in the lubricating agent usually is in the range from 2% to 25% by weight, based on the total lubricating grease, preferably in the range from 3% to 10% by weight. The concentration of the thickening components can be dependent on their characteristic thickening effect. For example, the strongly thickening acyloxy-substituted hydroxycarboxylic acids with higher acyloxy radicals ($C_{14}$-$C_{18}$) can be used in comparatively small amounts, while the alkoxy-substituted hydroxycarboxylic acids generally producing softer lubricating agents can be added in higher concentrations. Such natural laws can be applied as well to the use of mixtures of soaps.

Regular lubricating oil bases are used as liquid phases in the lubricating greases thickened according to the invention. Suitable are, for example, mineral lubricating oils, such as those with a petroleum base and/or synthetic lubricants based on a polyol ester, for example. The usual additives used in the lubricant technology such as additional lubricants, components to increase the load capacity, stabilizers, cleaning agents, etc. can be used in addition to the thickening agents according to the invention.

The invention therefor also resides in the improvement in the process for preparing lubricant greases comprising incorporating a sufficient amount of a lithium soap thickening agent into a lubricating oil to thicken the composition to a grease consistancy at room temperature, the improvement consisting essentially of using from 2% to 25% by weight, based on the final composition, of the lithium soaps of the invention, as said lithium soap.

The preparation of lubricating greases with an approx. 10% addition of lithium salts as thickening agent according to the invention is described in the following examples. Here the lubricating greases are prepared by saponification or formation of salt with lithium hydroxide, partly from the free hydroxycarboxylic acids with vicinal substitution and partly from the respective methyl esters. The lithium salts of 12-hydroxystearic acid and 9,10-dihydroxystearic acid are included as comparison products for the comparison in the subsequent tables.

The lubricating grease was formed by heating the mixture of mineral lubrication oil, lithium hydroxide monohydrate and hydroxycarboxylic acid in the amounts indicated to 100° C. with stirring for 15 minutes. Thereafter the mixture was heated to 200° C. with stirring, then cooled.

The analytical data of the lubricating greases include the values for the resting penetration and kneading penetration according to DIN 51804 as well as the dripping point according to DIN 51801. The following details apply:

RESTING PENETRATION DIN 51804

The sample is filled into the test vessel with the aid of a spatula, to prevent mechanical stress and the addition of air bubbles. The point of the quarter cone is adjusted with the penetrometer in such a manner that it barely touches the surface of the sample in the test vessel. The stop of the guide bar for the cone is loosened for a test period of 5 seconds so that the quarter cone can sink into the sample under the influence of its own weight. The depth to which it sinks is measured in tenths of a millimeter and subsequently recalculated for the cone penetration.

KNEADING PENETRATION DIN 51804

The lubricating greases are kneaded uniformly 60 times in one minute in a lubricating grease kneading machine, and the penetration is then mesured as described above.

DETERMINATION OF THE DRIPPING POINT DIN 51801

The sample is placed in a nipple and heated until it is sufficiently softened so that a drop falls from the nipple.

EXAMPLES

Lubricating greases with a respective 10% adddition of a thickening agent with a base of lithium salts of the following hydroxycarboxylic acids with vicinal substitution were prepared:

Example 1: epoxystearic acid, reacted with acetic acid

Example 2: epoxystearic acid, reacted with caprylic acid

Example 3: epoxystearic acid, reacted with capric acid

Example 4: epoxystearic acid, reacted with lauric acid

Example 5: epoxystearic acid, reacted with palmitic acid

Example 6: epoxystearic acid, reacted with stearic acid

Example 7: methyl epoxystearate, reacted with n-butanol

Example 8: methyl epoxystearate, reacted with ethylhexanol

Example 9: methyl epoxystearate, reacted with n-dodecanol

Comparison example 1: 9,10-dihydroxystearic acid

Comparison example 2: 12-hydroxystearic acid

The following compilation in table form contains the data about the nature of the acids that were used, the batch for the preparation of the lubricating grease (a mineral lubricating oil base was used in all cases) and the appearance as well as the analytical data of the obtained greases.

TABLE

| | Example 1 | Example 2 | Example 3 | Example 4 |
|---|---|---|---|---|
| Appearance of the acid | yellow-brown, turbid, highly viscous liquid | dark brown, slight turbid liquid product | dark brown, highly viscous liquid | light brown, clear liquid product |
| Acid number | 98.7 | 125 | 118.9 | 112 |
| MW | 567 | 448 | 471 | 500 |
| Batch sizes Amounts used of | | | | |
| Acid | 50 gm | 50 gm | 50 gm | 50 gm |
| LiOH . H$_2$O | 3.7 gm | 4.7 gm | 4.5 gm | 4.2 gm |
| Mineral lubricating oil | 433 gm | 433 gm | 433 gm | 433 gm |
| Appearance of the greases | viscous, homogeneous grease | yellow, soft homogeneous grease | very stiff, homogeneous grease | brown, stiff homogeneous grease |
| Analytical data for the greases | | | | |
| Resting penetration | | 411 | 191 | 193 |
| Kneading penetration | — | | 249 | 221 |
| Dripping point | | 163° C. | 161° C. | 173° C. |

| Example 5 | Example 6 | Example 7 | Example 8 | Example 9 |
|---|---|---|---|---|
| brown, solid product | brown, solid product | yellow, slightly turbid product | slightly yellow, slightly turbid, liquid product | dark brown, clear, liquid product |
| 106 | 98 | 169 | 156 | 125 |
| 528 | 571 | 331 | 359 | 448 |
| 50 gm | 50 gm | 50 gm | 50 gm | 50 gm |
| 4.0 gm | 3.7 gm | 6.34 gm | 5.85 gm | 4.7 gm |
| 433 gm | 433 gm | 433 gm | 433 gm | 433 gm |
| yellow, stiff homogeneous grease | yellow, stiff homogeneous grease | light-brown homogeneous, soft grease | yellow, homogeneous, soft grease | yellow-brown, homogeneous soft grease |
| 196 | 163 | 306 | 313 | 395 |
| 203 | 198 | 320 | 312 | |
| 156° C. | 156° C. | 186° C. | 156° C. | 158° C. |

| Comparison example 1 | Comparison example 2 |
|---|---|
| white, soft paste | white, stiff, scaly product |
| 166.1 | 196.0 |
| 337 | 285 |
| 50 gm | 50 gm |
| 6.23 gm | 7 gm |
| 433 gm | 433 gm |
| liquid, turbid, brown grease | stiff, pliant grease |
| | 278 |
| | 276 |
| | 197° C. |

The preceding specific embodiments are illustrative of the practice of the invention. It is to be understood however, that other expedients known to those skilled in the art or disclosed herein, may be employed without departing from the spirit of the invention or the scope of the appended claims.

We claim:

1. Lithium soaps of non-terminal vicinal substituted fatty acids having from 16 to 22 carbon atoms wherein said vicinal substituents are a hydroxy group and a group selected from the group consisting of alkanoyloxy having from 2 to 18 carbon atoms, alkenoyloxy having from 3 to 18 carbon atoms, and mixtures of said alkanoyloxy and said alkenoyloxy, said fatty acid being substituted with from 0 to 2 other hydroxyls.

2. The lithium soaps of claim 1 produced by epoxidation of fatty acids having from 16 to 22 carbon atoms and at least one ethylenic unsaturation, reaction of the resulting epoxy fatty acid with a reactant selected from the group consisting of alkanoic acid having from 2 to 18 carbon atoms, alkenoic acid having from 3 to 18 carbon atoms, and mixtures of said alkanoic acid and said alkenoic acid, and reaction with lithium hydroxide to form the lithium salt.

3. The lithium soaps of claim 2 wherein said lithium soaps are derived from naturally-occurring fatty acids.

4. The lithium soaps of claims 2 or 3 wherein said fatty acids having from 16 to 22 carbon atoms and at least one ethylenic unsaturation are selected from the group consisting of oleic acid, linoleic acid, linolenic acid, brassidic acid, ricinoleic acid and their lower alkyl esters.

5. The lithium soaps of claims 2, or 3 wherein said reactant is an alkanoic acid having from 10 to 18 carbon atoms.

6. A lithium soap having the formula

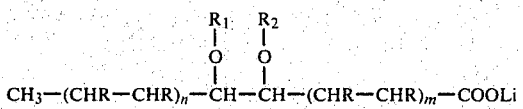

wherein R represents a member selected from the group consisting of hydrogen, hydroxy, a double bond with the adjacent R and mixtures thereof, n is an integer from 0 to 6, m is an integer from 0 to 6, n+m is an integer from 6 to 9, and $R_1$ and $R_2$ represents a member selected from the group consisting of hydroxyl, alkanoyl having from 2 to 18 carbon atoms and alkenoyl having from 3 to 18 carbon atoms, with the proviso that only one of $R_1$ or $R_2$ is hydroxyl and the further proviso that no more than 3 hydroxy groups or 2 double bonds are present.

7. A lithium soap of the reaction product of epoxidized oleic acid with an alkanoic acid having from 10 to 18 carbon atoms.

8. In the process for preparing lubricant greases comprising incorporating a sufficient amount of a lithium soap thickening agent into a lubricating oil to thicken the composition to a grease consistancy at room temperature, the improvement consisting essentially of using from 2% to 25% by weight, based on the final composition, of the lithium soaps of claims 1 or 2 as said lithium soap thickening agent.

9. The process of claim 8 wherein said lithium soaps were prepared in situ in the lubricant grease from the corresponding free acid or lower alkyl ester thereof.

10. The process of claim 8 wherein said lithium soaps are employed in an amount of from 3% to 10% by weight.

11. A lubricating grease consisting essentially of a liquid phase with lubricant characteristics, conventional lubricant additives in amounts from 0 to 25% by weight, and from 2% to 25% by weight of the lithium soaps of claims 1 or 2 as a lithium soap thickening agent.

12. The lithium soaps of claim 4 wherein said reactant is an alkanoic acid having from 10 to 18 carbon atoms.

* * * * *